United States Patent [19]

Matre

[11] Patent Number: 4,819,663

[45] Date of Patent: Apr. 11, 1989

[54] SITTING PATIENT LEG RESTRAINT

[76] Inventor: Rita Matre, 720 Judith Dr., Kettering, Ohio 45429

[21] Appl. No.: 115,464

[22] Filed: Apr. 11, 1989

[51] Int. Cl.$^4$ .............................................. A61F 13/00
[52] U.S. Cl. ................................................... 128/876
[58] Field of Search ............... 128/96, 87 R, 133, 134, 128/155, 160, 165, 168; 297/465–468, 485; 2/49 R

[56] References Cited

U.S. PATENT DOCUMENTS

| | | | |
|---|---|---|---|
| 134,489 | 0/0000 | Apotela | 128/90 |
| 2,005,294 | 6/1935 | Lazare | 128/134 |
| 2,435,311 | 2/1948 | Kimmell | 2/315 |
| 2,449,741 | 9/1948 | Fitzpatrick | 128/134 |
| 2,451,007 | 10/1948 | White | 297/485 |
| 2,739,642 | 3/1956 | Riedell | 297/485 |
| 3,100,484 | 8/1963 | Berl | 128/134 |
| 3,474,781 | 10/1969 | Gaylord, Jr. | 297/466 |
| 3,536,357 | 10/1970 | Murcott | 128/134 |
| 3,713,692 | 1/1973 | McCracken et al. | 297/467 |
| 4,050,737 | 9/1977 | Jordan | 128/134 |
| 4,108,170 | 8/1978 | Spann | 128/134 |
| 4,127,120 | 11/1978 | Applegate | 128/134 |
| 4,177,807 | 12/1979 | Ocel et al. | 128/133 |

Primary Examiner—Robert A. Hafer
Assistant Examiner—Charles H. Sam
Attorney, Agent, or Firm—Biebel, French & Nauman

[57] ABSTRACT

A sitting patient leg restraint comprises a central section, a hollow wide tube formed of cotton broadcloth or the like, elongated sufficiently as to be capable of looping around a thigh of the seated patient, and across the patient's mid-section (or lower torso) and around the sides at least to the back-rest of the chair. Tie straps of the same type of material extend from opposite ends of the central section. The interior of the central section is filled with a soft padding, such as cotton batting used in quilting, and the central section is divided into multiple sections by stitching or the like extending thereacross to assist in maintaining a relatively wide and flat shape, and to keep the padding secure and distributed throughout the interior. One end of the central section is located near a side of the chair back-rest, placed to extend along the patient's lower torso over the thigh-torso intersection into the groin area, thence under that thigh and back over the top of that thigh, across the lower torso and around the opposite side of the patient to the opposite side of the chair back-rest. The ties are then joined behind the back-rest.

1 Claim, 1 Drawing Sheet

SITTING PATIENT LEG RESTRAINT

BACKGROUND OF THE INVENTION

This invention relates to a device and method for holding or restraining handicapped patients in a sitting position. Many patients can benefit from spending some time in a sitting position, rather than being bedridden in supine position, but they do not have sufficient physical strength and/or stability to remain in a chair, wheelchair, or other chair-like device (hereinafter referred to collectively as a chair) without some form of belting and/or restraining system which will hold the patient's torso firmly and completely within the chair. Various forms of belts, folded sheeting, etc. have been improvised in an effort to achieve this desired result. Most of these have been makeshift and not suitable for use in more organized medical or nursing care facilities where some standard type of device is required for reason of procedure, as to assure approved restraining assistance to the patient which will not be potentially harmful in some way. In addition to adapting to a standard, such a device must also be of adequate strength, adjustable to different sizes of patient and/or chair, and launderable along with other reusable care items such as bedding, loose clothing, or the like. A simple seat belt type of restraint is not suitable because the patient may slip under it.

SUMMARY OF THE INVENTION

The present invention provides a restraining system (e.g. a device and a method) which can meet these criteria, which can be easily and inexpensively manufactured, which does not need complicated buckles or similar connecting apparatus, and which can be applied by non-professional personnel without concern for possible consequent harm to and/or insecurity of the seated patient.

The device according to this invention includes a central section elongated sufficiently as to be capable of looping around at least one thigh of the seated patient, and across the patient's mid-section (or lower torso) and around the sides at least to the back-rest of the chair. Preferably this central section is a hollow wide tube formed of cotton broadcloth or the like which has fastened to its opposite ends tie straps of the same type of material. The interior of the central section is filled with a soft padding, such as cotton batting used in quilting, and the central section is divided into multiple sections by stitching or the like extending thereacross to assist in maintaining a relatively wide and flat shape, and to keep the padding secure and distributed throughout the interior.

The device is used by seating the patient in a chair and applying the device as follows. One end of the central section is located near a side of the chair backrest, and then placed to extend along the patient's lower torso over the thigh-torso intersection into the groin area, thence under that thigh and back over the top of that thigh, across the lower torso and around the opposite side of the patient to the opposite side of the chair back-rest, where the opposite end of the central section is located. The ties are then joined behind the back-rest, preferably simply by securely tying them together.

The device can be positioned to encompass either thigh of the seated patient. In practice, it has been found that the loop around one thigh is sufficient, and that with the device so applied the patient is held with the buttocks against the hair back-rest and firmly on the seat, restrained against lateral movement of the lower torso. The force applied to the patient by the device is distributed because of the width of the device and as a result of its padding, so as not to cause local sores or the like.

Accordingly, the primary object of this invention is to provide a simple effective leg restraint device for helping to hold a disabled patient in a sitting position within a chair or the like; an additional object is to provide a method of restraint and support for sitting patients which is comfortable, effective, and easy to use.

Other objects and advantages of the invention will be apparent from the following description, the accompanying drawings and the appended claims.

DESCRIPTION OF THE PREFERRED EMBODIMENT

Figure 2:
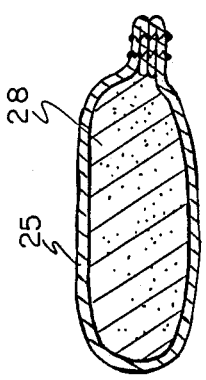
FIG. 2 is an enlarged cross-sectional view taken on line 2—2 in FIG. 1.
Figure 1:
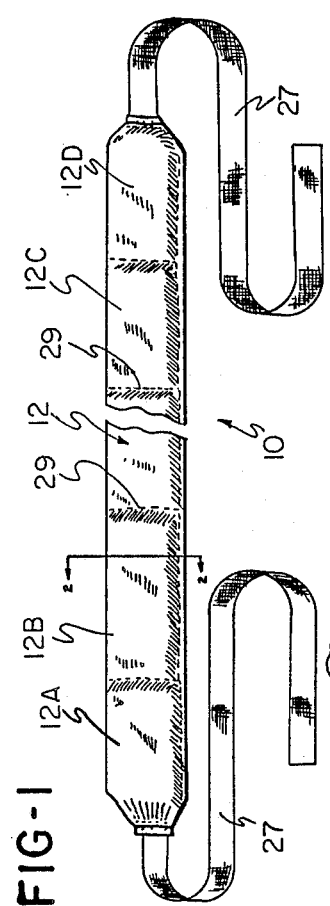
FIG. 1 is an elevational view of a restraint device according to the invention, with a break to shorten the overall length of the view.

In accordance with the invention a restraint device 10 is illustrated in FIG. 1 as including a central section 12 elongated sufficiently as to be capable of looping around a thigh 14 of the seated patient 15, and across the patient's mid-section (or lower torso) 16 and around the sides at least to the back-rest 20 of the chair 22. Preferably this central section 12 is formed as a hollow wide tube 25 (see FIG. 2) of cotton broadcloth or the like which has fastened to its opposite ends tie straps 27 of the same type of material. The interior of the central section is filled with a soft padding 28, such as cotton batting used in quilting, and the central section is divided into multiple sections 12A, 12B, 12C etc. by stitching or the like 29 extending thereacross to assist in maintaing a relatively wide and flat shape, and to keep the padding secure and distributed throughout the interior.

The device is used by seating the patient in a chair 22 and applying the device 10 as follows. One end 12A of the central section 12 is located near a side 20A of chair back-rest 20, and then the device is routed along the patient's lower torso over the thigh-torso intersection into the groin area, thence under the thigh 14 and back over the top of that thigh, across the lower torso 16 and around the opposite side of the patient to the opposite side 20B of the chair back-rest, where the opposite end 12D of the central section is located. Tie straps 27 are then joined behind the backrest 20, preferably simply by securely tying them together.

Figure 5:
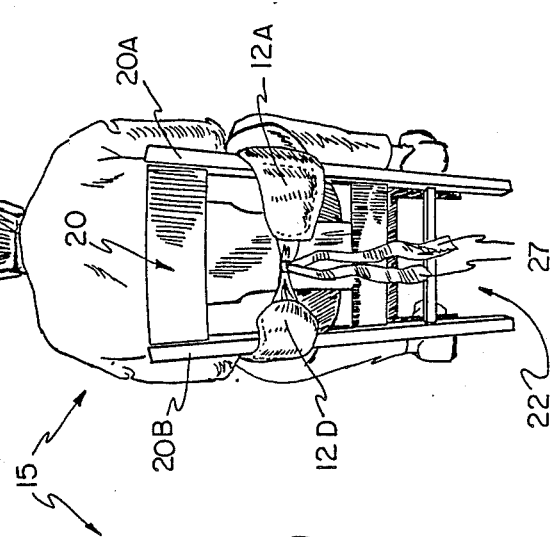
FIGS. 4 and 5 are front and rear views, respectively, of the seated patient with the device applied.
Figure 4:
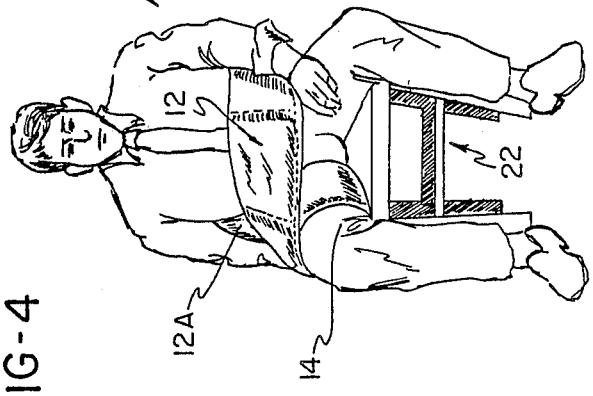
Figure 3:
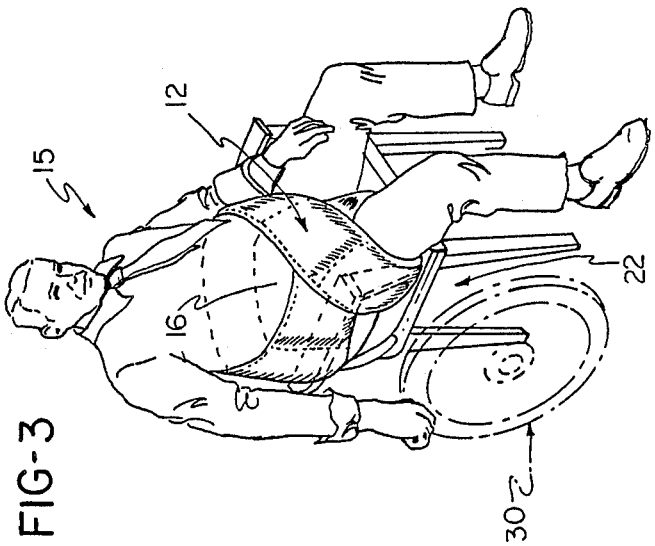
FIG. 3 is a perspective view of a patient seated in a chair with the device applied to the patient.

The device 10 can be positioned to encompass either thigh of the seated patient. In practice, a loop around one thigh is sufficient, as shown in FIGS. 3–5, and with the device so applied the patient is held with the buttocks against the chair back-rest and firmly on the seat, restrained agaist lateral movement of the lower torso. The force applied to the patient by the device is distributed along the width of the device and as a result of its padding, so as to minimize chafing or the like.

A specific device, successfully tested, has a central section 10 which is seventy inches in length, divided into six parts 12A, 12B etc. of approximately equal length. The central section has a width of about seven inches and an compressed thickness of about three-quarters of an inch. The end parts of the central section are preferrably tapered somewhat (see FIG. 1) where they are attached to the ties 27. Those ties have a length of about thirty six inches. A device of these approximate dimensions has been found to accomodate sufficient variations in patient size and chair or other seating devices, as to be widely applicable. An outline of a wheel 30 is shown in FIG. 3 to illustrate that the invention is applicable to patients in a wheelchair as well as stationary chairs.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is deinfed in the appended claims.

What is claimed is:

1. A method of holding a patient in a sitting position upon a chair or the like, comprising
   providing a restraint device having an elongated padded central section with a width sufficient to distribute restraining pressure over a substantial area,
   and
   tie means attached to opposite ends of the central section,
   wrapping the restraint device about the mid-section and sides of a patient's torso and looping the central section around one thigh of the patient, then connecting the tie means behind the chair to restrain the patient fully into the chair in a generally upright seated position with the patient's thighs extending approximately at right angles to the patient's torso.

* * * * *

UNITED STATES PATENT AND TRADEMARK OFFICE
CERTIFICATE OF CORRECTION

PATENT NO. : 4,819,663
DATED : April 11, 1989
INVENTOR(S) : Rita Matre

It is certified that error appears in the above-identified patent and that said Letters Patent is hereby corrected as shown below:

Title page, line 5 "Filed: Apr. 11, 1989" should read

--Filed: Oct. 30, 1987--

Signed and Sealed this

Twenty-third Day of January, 1990

*Attest:*

JEFFREY M. SAMUELS

*Attesting Officer*     *Acting Commissioner of Patents and Trademarks*